United States Patent [19]

Colling

[11] Patent Number: 5,258,745
[45] Date of Patent: Nov. 2, 1993

[54] SYSTEM AND METHOD FOR PREDICTION OF TIMES OF VOIDING UTILIZING TEMPERATURE MEASUREMENTS

[76] Inventor: Joyce C. Colling, 10185 SW. View Ter., Tigard, Oreg. 97224

[21] Appl. No.: 13,125

[22] Filed: Feb. 3, 1993

Related U.S. Application Data

[63] Continuation of Ser. No. 813,213, Dec. 23, 1991, abandoned.

[51] Int. Cl.⁵ ............................................. G08B 21/00
[52] U.S. Cl. .................... 340/573; 128/885; 128/886; 340/584; 340/604
[58] Field of Search ............... 340/573, 604, 584, 585; 128/886, 885, DIG. 25

[56] References Cited

U.S. PATENT DOCUMENTS

| | | | |
|---|---|---|---|
| 3,460,123 | 8/1969 | Bass | 340/573 |
| 4,205,671 | 6/1980 | Lassen | 340/573 |
| 4,271,406 | 6/1981 | Wilson | 340/604 |
| 4,356,479 | 10/1982 | Wilson | 340/604 |
| 4,539,559 | 9/1985 | Kelly et al. | 340/573 |
| 4,653,491 | 3/1987 | Okada et al. | 128/886 |
| 4,738,260 | 4/1988 | Brown | 128/886 |
| 4,800,370 | 1/1989 | Vetecnik | 340/573 |
| 4,977,906 | 12/1990 | Di Scipio | 128/886 |

Primary Examiner—Glen R. Swann, III
Attorney, Agent, or Firm—Stoel Rives Boley Jones & Grey

[57] ABSTRACT

A temperature sensor (10), which is connected to a sampling/recording meter (14), is imbedded in a diaper (22). The meter measures and records the temperature of the sensor at time intervals of, for example, one minute over a predetermined period of, for example, three days. The temperature and time data are then loaded from the meter to a computer (30), which causes a printer (40) to plot temperature versus time data in graphical format, and numerical format. Voiding events are identified. Thereafter, at a short time before the person will void, the person can voluntarily use a toilet or bed pan either alone or with the assistance of care giver. This voluntary voiding is an example of intervention. The meter includes an event button (44) that allows the recording and later printing of a symbol representing a specific event and the time the event occurred. The symbols may be used in identifying voiding events.

13 Claims, 2 Drawing Sheets

SYSTEM AND METHOD FOR PREDICTION OF TIMES OF VOIDING UTILIZING TEMPERATURE MEASUREMENTS

STATEMENT OF GOVERNMENT INTEREST

This invention was made with government support under NIH Grant NR-01554, "Patterned Urge Response Toileting for Incontinence" (Urinary Incontinence Monitor), ID# OHSU 90 D# 171, awarded by the National Institute of Health. The Government has certain rights in the invention.

This is a continuation of application Ser. No. 07/813,213, filed Dec. 23, 1991, now abandoned.

FIELD OF THE INVENTION

The present invention relates to a system and method for accurately predicting approximate times an incontinent person without intervention would void in the future.

BACKGROUND OF THE INVENTION

Incontinent persons often urinate or void in a diaper or clothing rather than in a toilet causing significant discomfort and distress to the person. In addition, there is considerable expense to nursing homes for changing the diaper or clothing as well as providing these disposable supplies. The costs for such supplies and services has been estimated at 3 billion dollars per year.

Various devices have been invented to indicate when a person voids so that the person's diaper or clothing may be changed. For example, U.S. Pat. Nos. 3,460,123 of Bass, 4,271,406 of Wilson, 4,356,479 of Wilson, 4,539,559 of Kelly et al., 4,738,260 of Brown describe systems that set off an alarm after a person being monitored voids. These systems include circuits that are closed through urine. See U.S. Pat. Nos. 3,460,123 (conductor screens 30 and 32); 4,271,406 (moisture sensing electrodes 30); 4,356,479 (magnetic sensing electrodes 30); 4,539,559 (absorbent pad 2); 4,738,260 (urine sensing pad 12 and sheath 102; col. 3, lines 6-7, col. 5, lines 6-8).

U.S. Pat. No. 4,800,370 of Vetecnik describes a wetness detection system that detects dampness in a diaper or other clothing and triggers an alarm when a conductive path between conductor wires 224 is closed. The Vetecnik patent also describes an additional feature that provides a reading of the patient's temperature or "body heat." See col. 3, lines 63-65 and col. 5, lines 27-30. As shown in FIG. 3, detector/transmitter 4 is attached between the skin of a person 308 and a diaper 300 by a spring clip 204. The temperature of the skin is measured by means of a thermistor 412 (shown in FIG. 4) located inside housing 200 of detector/transmitter 4 (shown in FIG. 2). The temperature of the urine is not measured because the urine is located away from housing 200. Note that elongated conductor strip 216 (shown in FIGS. 2 and 4) travels down the diaper toward the location of the urine.

U.S. Pat. No. 4,653,491 of Okada et al. describes a system that measures the amount of wetness in a diaper by measuring capacitance. When the capacitance exceeds a limit, an alarm is set off.

A problem with the systems of each of above-cited patents is that they determine only the occurrence of urination after it has happened. The systems do not help the incontinent person to avoid the situation.

U.S. Pat. No. 4,977,906 of DiScipio describes a system including sensors 12 and 13, which are placed in an undergarment, such as a diaper. During an enuresis incidence, moisture is absorbed in the undergarment. When the undergarment is sufficiently wet, the open circuit across sensors 12 and 13 is completed resulting in an alarm being set off. The DiScipio patent states it is possible to monitor occurrences of urine discharge and determine when future occurrences are likely. The information can be used to forewarn the patient of the likelihood of a enuresis incident.

A problem with the system of the DiScipio patent is that as long as the diaper remains wet, the open circuit across sensors 12 and 13 remains completed. The system cannot recognize the situation when a person voids twice before the diaper is dry. Therefore, the predictive value of the system is limited.

There is, therefore, a need for a system that can detect urination even though the diaper of the person is wet.

SUMMARY OF THE INVENTION

It is, therefore, an object of the invention to provide a method and system for detecting voiding in an undergarment whether or not the undergarment is still wet from a previous voiding.

Another object of the invention is to provide a method and system for predicting the times of future voiding by a person by periodically sampling the temperature obtained by a sensor which is over a long period of time placed near the urethral opening of the person.

Still another object of the invention is to provide a system with an event button that when activated records a symbol that can later be used to indicate times a person voided and whether the voiding occurred in the undergarment or a toilet.

The present invention relates to a system and method for accurately predicting approximate times an incontinent person without intervention would void in the future. A temperature sensor, which is connected to a sampling/recording meter, is imbedded in a diaper. The meter measures and records and stores the temperature of the sensor at time intervals of, for example, one minute over a predetermined period of, for example, three days. The temperature and time data are then loaded from the meter to a computer, which causes a printer to plot temperature versus time data in graphical format. A pattern of voiding events are identified and a voiding schedule is constructed for the person based on his usual voiding times. Thereafter, at a short time before the person will void, the person can voluntarily use a toilet or bed pan either alone or with the assistance of care giver. This voluntary voiding is an example of intervention. The meter includes an event button that allows the recording and later printing of a symbol representing a specific event and the time the event occurred. The symbols may be used in identifying voiding events.

DETAILED DESCRIPTION OF PREFERRED EMBODIMENT

People often urinate at very near the same times every day. The times at which such a person urinates may be predicted by use of the present invention. The person may voluntarily void in a toilet or bed pan shortly before the predicted times of voiding. A care giver may assist the person in voiding in a toilet or bed pan. In this regard, it is expected that the invention will be used primarily by incontinent people. However, the invention also may be used by those people who are continent but that through some physical problem have difficulty in urinating in a toilet or bed pan without help. Many, but not all, of the persons using the invention will be older persons in nursing homes or at home who are receiving assistance from care givers.

Figure 1:
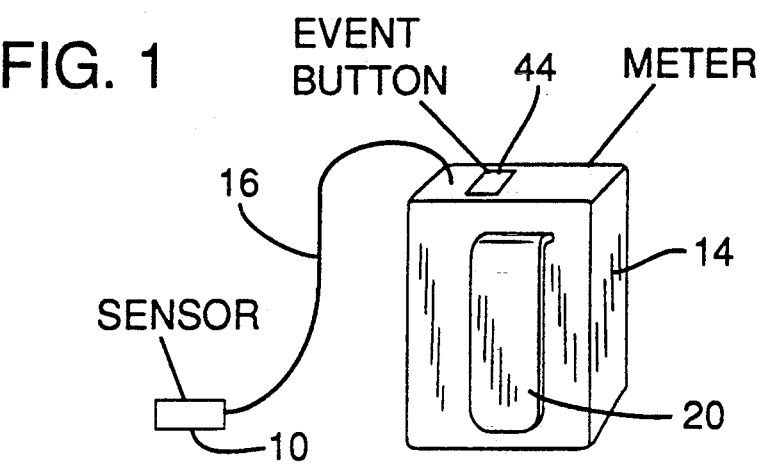
FIG. 1 shows the temperature sensor and sampling/recording meter of the present invention.
Figure 2:
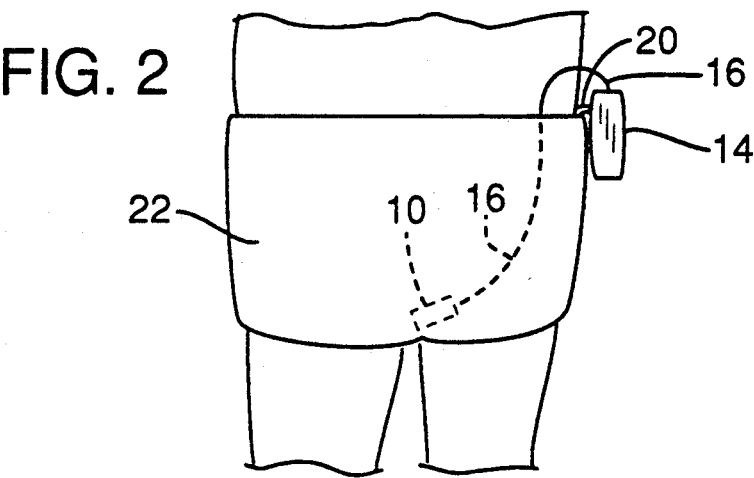
FIG. 2 shows placement of the temperature sensor and sampling/recording meter in operation.

Referring to FIG. 1, the present invention includes a temperature sensor 10 that is connected to a sampling-/recording meter 14 via conductors 16. Referring to FIG. 2, in operation, meter 14 is attached by clip 20 to an undergarment, such as diaper 22. As used herein, "undergarment" means a diaper, underpants, pad, or other article of clothing suitable to be worn around the waist and legs of a person. The undergarment includes a region that is near the urethral opening of the person when the undergarment is worn. Sensor 10 is placed near the region such that sensor 10 will be in direct contact with or close to discharged urine. Sensor 10, shown in dashed lines, is embedded in or otherwise secured to or placed next to diaper 22.

Meter 14 records the temperature of sensor 10 at time intervals of, for example, one minute over a predetermined period of, for example, three days. After temperature samples have been taken for the predetermined period, the temperature and time data are down loaded from meter 14 to a computer 30, shown in FIG. 3. Under the command of computer 30, printer 40 plots the temperature versus time data sampled and recorded by meter 14. The plotted data is analyzed to determine at what times of day the person regularly voids. Thereafter, at a short time before the person will void, the person can voluntarily use a toilet either alone or with the assistance of care giver.

Figure 4:
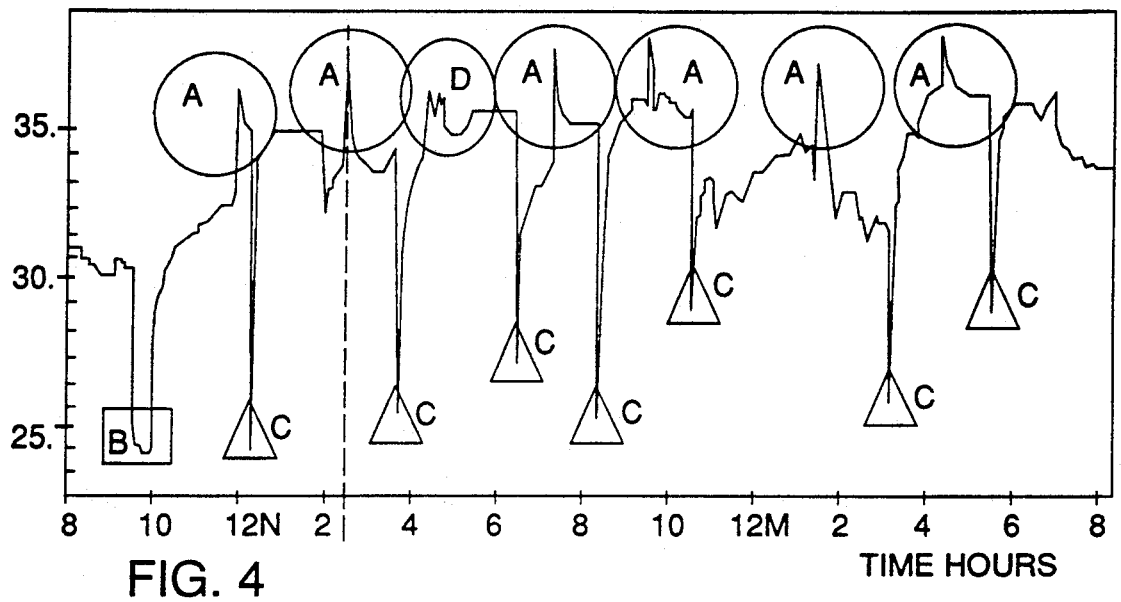
FIG. 4 shows exemplary temperature vs. time data, which is printed by the computer.

The operation of sensor 10 and the sampling and recording feature of meter 14 is illustrated by FIG. 4, which shows exemplary plotted temperature vs. time data plotted by printer 40. The temperature vs. time data was sampled and recorded by meter 14 over a twenty-four hour period. The temperature shown in FIG. 4 is the temperature sensed by sensor 10 and measured by meter 14. In FIG. 4, "A" indicates a voiding event; "B" indicates diaper 22 was removed for a morning bath; "C" indicates diaper 22 was removed for changing; and "D" indicates a bowel movement.

At 8:00 AM, when the samples begin, diaper 14 is dry and the temperature sensed by sensor 10 is about 31 degrees Celsius (° C.). Diaper 22 remains dry and the temperature remains at around 31° C. until about 9:30 AM, when diaper 22 is removed during the person's bath. When diaper 22 is removed, sensor 10 senses and meter 14 measures ambient air temperature. At slightly before 10:00 AM, the same or a different diaper is put back on the person and meter 14 makes additional temperature measurements.

From about 10:00 AM to about 11:45 AM, the measured temperature increases from about 30° C. to 32.5° C. The measured temperature can change by a relatively large amount even though there is no voiding because of changes of body temperature, heat caused by movement of diaper 22 against the skin the person, and changes in the position of sensor 10 with respect to the skin of the person.

At about 11:50 AM, the temperature sensed by sensor 10 rapidly increases to about 36° C. and then quickly decreases over approximately the next fifteen minutes to about 35° C. The plotted samples from about 11:50 AM to 12:05 PM are circled and marked with an "A." Temperature versus time samples having this type of rapid rise and slower decrease in temperatures typically indicate a voiding episode. Shortly after about 12:05 PM, when diaper 22 is removed, sensor 10 senses ambient air temperature. The time during which the diaper is removed is denoted by a triangle and the letter "C."

After diaper 22 is put back on the person the measured temperature shoots back up to about 35° C. and remains there from about 12:30 PM to 2:00 PM. Even though the temperature is relatively high from about 12:30 to 2:00 PM, the flatness of the temperature data indicates the lack of voiding. It is likely that sensor 10 was close to the skin of the person from about 12:30 PM to 2:00 PM and, therefore, picked up a relatively large amount of body temperature. 35° C. is close to the body temperature of 98.6° F. By contrast, from about 8:00 AM to 9:30 AM, sensor 10 was probably positioned farther from the body and, therefore, measured a lower temperature.

At about 2:30 PM, there is another voiding episode which is indicated by a sharp temperature peak and subsequent declining temperature. A vertical line is shown at about 2:30 PM, which is initiated by activation of event button 44, shown in FIG. 1 and described below. After the diaper is changed at about 3:40 PM, the measured temperature steadily increases until there are two small peaks at about 36° C. from about 4:15 to 4:30 PM. The peaks represent a bowel movement, and are uncharacteristic of urination. The bowel movement is indicated by a circled letter "D." At about 6:15 PM, the diaper is changed.

There are additional times of voidings, which are circled and marked with an "A" at about 7:15 PM, 9:45 PM, 1:45 AM, and 4:30 AM.

The following is a method for determining when voiding events occurred by observing the temperature vs. time data plotted on FIG. 4. First, voiding events are characterized by sharp spikes of, for example, as much as 2 or 3 degrees in temperature. The sharp spikes are followed by a gradual decline in temperature toward the temperature prior to the voiding event. However, movement by the person wearing the diaper can change the temperature measured by sensor 10.

The method of prediction can be performed by inspection and hand plotted. Alternatively, or in addition, the times could be predicted by computer 30 under an algorithm that follows the procedure described above.

In addition to the rules disclosed above, notes may be taken by the nurse or person under test of each time the diaper is changed when there has been voiding and when there has not been voiding. Also, the person under test can note each time they urinate. In this respect, an event button 44 on meter 14 may be activated, which causes a particular symbol to be recorded in meter 14. The symbol may be vertical lines that are printed on the graph of FIG. 4. For example, a single vertical line is shown on FIG. 4 at about 2:30 PM. When event button 44 is activated once at a given time, one vertical line should are printed for that time. When event button 44 is activated twice in a short time, two vertical lines are printed for that time. Alternatively, meter 14 could include a different event button for each type of event.

Event button 44 may be used to indicate various events. For example, activating event button 44 once can be used to indicate voiding in diaper 22. Activating event button 44 twice within a very short time period can indicate voiding in a toilet or bed pan. Activating event button 44 three times can indicate a care giver removed a diaper that did not contain urine or a stool. Activating event button 44 four times can indicate a bowel movement. Of course, The vertical line(s) produced in response to activation of event button 44 are only helps in deciding whether a voiding event as occurred. The person under test or the care giver can forget to or otherwise fail to activate event button 44 at the appropriate time.

Figure 5:
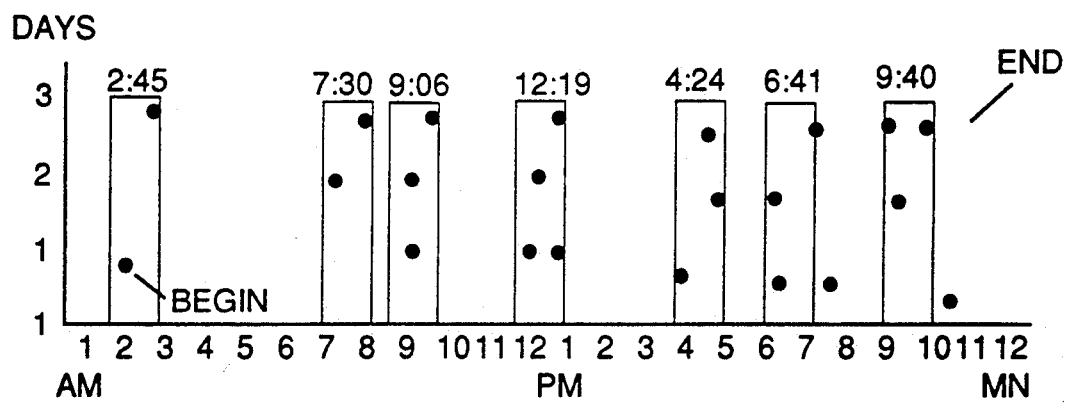
FIG. 5 shows composite analyzed temperature vs. time data.

The accuracy of the prediction of voiding events may be increased by compiling data similar to that in FIG. 4 over several, for example, three days. FIG. 5 shows such a compilation. Referring to FIG. 5, black dots show the time of voiding for each of three days. The times of voiding in day 1 are shown as dots beneath the dots representing times of voiding in day 2, which in turn are beneath the dots representing times of voiding in day 3. Rectangles having a width corresponding to about one hour are drawn around clusters of dots. The placement of the rectangles is not an exact science but, as can be seen in the case of FIG. 5, the choice for placement of the rectangles is reasonably clear. The numbers on the top of the rectangles are the mean times of the times represented by the dots in the rectangles.

Predicting the time of voiding based on the mean time or any other such time is a prediction of an approximate time of voiding. Nevertheless, the prediction under the method of the present invention can be quite accurate in the cases of many people. The time of voiding may be thought of as a range rather than an approximate time, where the size of the range is a function of the accuracy of the approximate time. For example, about 85% of persons without voluntary control who were tested consistently voided within 30 minutes of mean time.

The time at which the person should voluntarily void with or without the help of others may be calculated under several methodologies. For example, a preferred time to voluntarily void is sometime between one-half hour before the mean time and the mean time of a cluster of voiding times within a rectangle, with the time preferably being closer to one-half hour before. Under other methods, the time to void is at the time of the beginning of the rectangle or a predetermined amount of time, e.g., 10 minutes, before the first voiding of a cluster of voidings. Voluntary voiding is an example of intervention. Another example of intervention is a significant change in the amount or time of intake of food, liquids, or drugs, or significant change in activity.

Initial study suggests that voluntary voiding does not change the time of future voiding. In the case of some persons, however, voluntary voiding may alter times of consumption of fluids and voiding enough to cause the predicted times to no longer be accurate. In that case, the procedure of the invention could be repeated.

An example of meter 14 is the Rustrak Ranger manufactured by Gulton Industries, Inc. of East Greenwich, Road Island. The Rustrak Ranger was designed to sample temperature changes in industry where remote temperature monitoring is desirable. For example, the Rustrak Ranger has been used in monitoring the refrigeration temperature of perishables during transport via truck or train.

Figure 6:
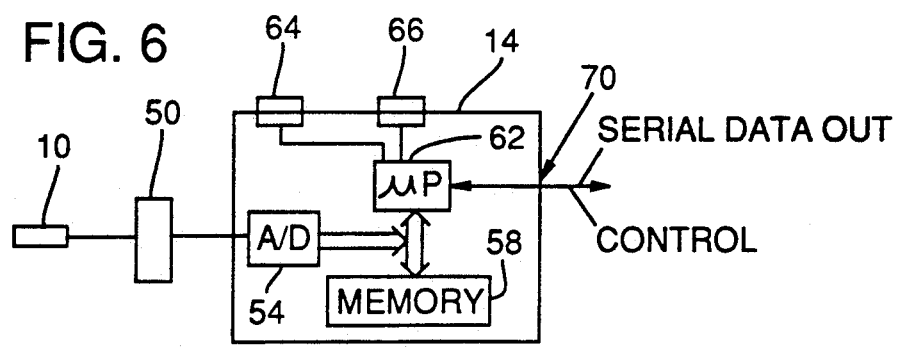
FIG. 6 shows details of one example of the sampling/recording meter.

Referring to FIG. 6, a block diagram of the Rustrak Ranger is shown with sensor 10 connected to meter 14 through signal conditioning pod 50, which is also sold by Gulton Industries. Pod 50 includes four channels that may receive signals from sensors that measure and convert phenomena such as temperature, pressure, flow, voltage, current, etc., into analog signals representing the phenomena. For the present invention, only temperature is measured. Pod 50 converts the signal from sensor 10 into a standard signal level (zero to 2 volts, full scale) suitable for input to meter 14. Of course, meter 14 could be designed to accept signals directly from sensor 10 without pod 50.

Meter 14 includes analog to digital (A-to-D) converter 54 that receives data from pod 50. Data from A-to-D converter 54 is stored in memory 58 under the control of microprocessor 62. Select button 64 and enter button 66 control microprocessor 62. Enter button 66 is an example of event button 44.

Figure 3:
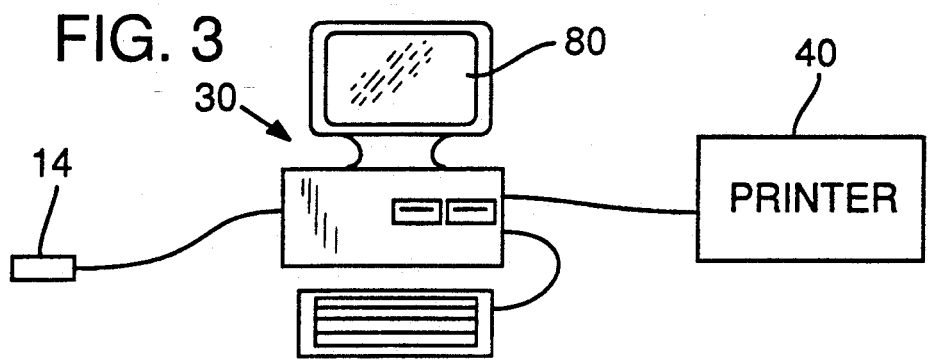
FIG. 3 shows the sampling/recording meter down loading information to a computer, and a printer for printing information from the computer.

The Rustrak Ranger is designed to be compatible with IBM PC computers. Referring to FIGS. 3 and 6, temperature data is loaded from microprocessor 62 to computer 30 through serial data output 70. Output 70 is connected to the RS-232 port of computer 30. The Rustrak Ranger is designed to be used with software called Pronto which is available from Gulton Industries, the manufacturer of the Rustrak Ranger. Pronto controls data transfer from output 70 to computer 30.

Pronto allows presentations of the temperature vs. time data in a variety of formats. For example, the temperature vs. time data may be displayed on monitor 80 of computer 30 or printed by printer 40, which may be an Epson printer. The data may be printed in graphical format as in FIG. 4 or as numerical values arranged in six columns. Column 1 includes the date, minute, and second the temperature sample was taken (e.g., 12:11:05:30); column 2 lists the temperature when the sample was taken (e.g. 35.34); column 3 lists the average between the current and previous temperature; column 4 lists the maximum temperature during the minute indicated in column 1; column 5 lists the minimum temperature during the minute indicated in column 1; and column 6 indicates whether any "events" were noted (i.e., whether event button 44 was pushed one or more times).

In the preferred embodiment, the time vs. temperature data of FIG. 4, which is plotted by printer 40, is generated only from the time data of column 1 and the temperature data of column 2; not from the data in columns 3, 4, and 5. A vertical line is preferably printed on the temperature vs. time graph of FIG. 4 for each time in which there is event data in column 6.

In the present invention, the temperatures measured by sensor 10 are typically within the range of roughly 18° to 45° C. The Rustrak Ranger is designed to be used with sensors 10 that measure temperature over a much wider range. For example, sensor 10 may be a thermistor with a temperature range of −40° to +110° C., in which case, pod 50 should be of the POD-03 type, as supplied by Gulton Industries. The Rustrak Ranger (i.e., meter 14) is adjustable for different temperature ranges and should be set appropriately for the range of the present invention. An example of the thermistor is 400 series temperature sensor, # 081-440004-NA-FP-72-ST, marketed by Yellow Springs Instrument Co. of Yellow Springs, Ohio. Alternatively, sensor 12 may be a thermocouple (type J) with a temperature range of 0° to 400° C., in which case, pod 50 should be of the POD-06 type.

Another example of meter 14 is the Vitalog PMS-8 manufactured by Vitalog Corporation, which might be no longer in business. The PMS-8, which is relatively expensive, was designed to make measurements of physiological data.

Alternatively, rather than use a commercially constructed meter such as the Rustrak Ranger or PMS-8, meter 14 could be especially designed to perform the functions of the present invention. Likewise, the functions performed by Pronto could easily be performed by especially written software. The meter would ideally be no larger than about 2"×3"×1" (5.1 cm×7.6 cm×2.4 cm), and weight no more than 3 to 4 ounces (86 grams to 114 grams). In addition, meter 14 would be able to be easily operated by people having little manual dexterity and technical training.

In the preferred embodiment, clip 20 clips meter 14 to diaper 22. By contrast, meter 20 could be placed on a table or included in other equipment.

The temperature, time, and event data may be made at the person under test's home, or in a medical clinic, hospital, or nursing home. It is expected that the data will be analyzed by experienced personnel in lab and the results sent back to the person. The system and software could be purchased or rented with some instruction for analysis by a professional or for self analysis. The temperature vs. time data would be more secure and portable if the data logger had the ability to sort data on a ROM or RAM disk. Once the data were collected, a nurse could simply remove the disk and send it to a lab for analysis. Later the disk could be stored in the patient's medical file for future reference.

The undergarment may be a commercially available absorbent pad or diaper containing an embedded wire attached sensor 10 at one end and a plug in connector at the other end which attaches to meter 14 or pod 50. Tape or a velcro fastener may be used to hold the wire in place within the undergarment.

Those skilled in the art will appreciate that many changes may be made in the above-described details of the preferred embodiment of the present invention without departing from the underlying principles thereof. The scope of the present invention should be determined, therefore, by the following claims.

I claim:

1. A system for accurately determining times a person voided during a period, the system comprising:
   an undergarment including a region that is near the urethral opening of the person when the undergarment is worn;
   a temperature sensor positioned near the region of the undergarment;
   measuring means operationally connected with the temperature sensor for measuring temperatures sensed by the temperature sensor at times throughout multiple one of the period; and
   storing means for storing values representing the measured temperatures and the respective times of measurement.

2. The system of claim 1 further comprising a computer means for receiving data representing the measured temperature and times of measurements and for organizing the data for presentation in graphical and numerical format.

3. The system of claim 1 further comprising event button means for producing an event signal each time the event button means is activated, and event recording means for recording the event signal and the times of production of the event signal.

4. The system of claim 3 further comprising a computer means for receiving data representing the measured temperatures, times of measurement, and event signal data representing the event signal and the times of the production of the event signals, and for organizing the data representing the measured temperatures, times of measurement, and event signal data for presentation in graphical format.

5. The system of claim 1 further comprising first and second event button means for producing respective first and second event signals in response to activation of the respective first and second event button means.

6. The system of claim 5 further comprising a computer means for receiving data representing the measured temperatures, the respective times of measurement, and the first and second event signal, and analyzing means for analyzing the data to predict approximate times of the day the person without intervention would void.

7. The method of claim 1 in which the undergarment contains an embedded wire having two ends, the wire being attached to the temperature sensor at one end and a plug-in connector at the other end.

8. A system for accurately determining times a person voided in an undergarment during a period, the undergarment including a region that is near the urethral opening of the person when the undergarment is worn, the system comprising:
   a temperature sensor positionable near the region of the undergarment;
   measuring means operationally connected with the temperature sensor for measuring temperatures sensed by the temperature sensor at times throughout multiple ones of the period; and
   storing means for storing values representing the measured temperatures and the respective times of measurement.

9. The system of claim 8 further comprising a computer means for receiving data representing the measured temperatures and times of measurements and for organizing the data for presentation in graphical and numerical formats.

10. The system of claim 8 further comprising event button means for producing an event signal each time the event button means is activated, and event recording means for recording the event signal and the times of production of the event signal.

11. The system of claim 10 further comprising a computer means for receiving data representing the measured temperatures, times of measurement, and event signal data representing the event signal and the times of the production of the event signals, and for organizing the data representing the measured temperatures, times of measurement, and event signal data for presentation in graphical format.

12. The system of claim 8 further comprising first and second event button means for producing respective first and second event signals in response to activation of the respective first and second event button means.

13. The system of claim 12 further comprising a computer means for receiving data representing the measured temperatures, the respective times of measurement, and the first and second event signal, and analyzing means for analyzing the data to predict approximate times of the day the person without intervention would void.

* * * * *